United States Patent
Norby et al.

(10) Patent No.: US 8,426,077 B2
(45) Date of Patent: Apr. 23, 2013

(54) PROTON CONDUCTORS

(75) Inventors: Truls Norby, Oslo (NO); Reidar Haugsrud, Oslo (NO); Stefan Marion, Høvik (NO); Mari-Ann Einarsrud, Trondheim (NO); Kjell Wiik, Trondheim (NO); Øystein Andersen, Trondheim (NO); Ruth Astrid Strøm, Trondheim (NO); Tor Grande, Trondheim (NO)

(73) Assignee: Universitetet I Oslo, Oslo (NO)

( * ) Notice: Subject to any disclaimer, the term of this patent is extended or adjusted under 35 U.S.C. 154(b) by 1073 days.

(21) Appl. No.: 11/722,233

(22) PCT Filed: Dec. 22, 2005

(86) PCT No.: PCT/EP2005/013873
§ 371 (c)(1),
(2), (4) Date: Sep. 24, 2007

(87) PCT Pub. No.: WO2006/066918
PCT Pub. Date: Jun. 29, 2006

(65) Prior Publication Data
US 2009/0104500 A1    Apr. 23, 2009

(30) Foreign Application Priority Data
Dec. 23, 2004 (NO) .................................. 20045639

(51) Int. Cl.
*H01M 8/10* (2006.01)
(52) U.S. Cl.
USPC ........................................ 429/479; 429/491

(58) Field of Classification Search .................... 429/465
See application file for complete search history.

(56) References Cited

U.S. PATENT DOCUMENTS

| | | | |
|---|---|---|---|
| 3,758,486 A | 9/1973 | Ropp | |
| 4,225,653 A | 9/1980 | Brixner | |
| 5,314,508 A * | 5/1994 | Taniguchi et al. | 29/623.5 |
| 6,258,486 B1 | 7/2001 | Fauteux et al. | |
| 6,620,750 B2 | 9/2003 | Kim et al. | |
| 2001/0055717 A1 | 12/2001 | Fauteux et al. | |

(Continued)

FOREIGN PATENT DOCUMENTS

| | | |
|---|---|---|
| CN | 1539739 | 10/2004 |
| CN | 1539747 | 10/2004 |

(Continued)

OTHER PUBLICATIONS

Imanaka, et al.; Title: "Rare Earth Contribution in Solid State Electrolytes, Especially in the Chemical Sensor Field," Journal of Alloys and Compounds, Elsevier Dequoia, Lausanne, CH, vol. 250, Mar. 20, 1997, pp. 492-500.

(Continued)

*Primary Examiner* — Ula C Ruddock
*Assistant Examiner* — Jacob Marks
(74) *Attorney, Agent, or Firm* — Sutherland Asbill & Brennan LLP

(57) ABSTRACT

Proton conductivity has been shown in acceptor-doped rare earth orthoniobates and tantalates ($LnNbO_4$ and $LnTaO_4$) at high temperatures and in a humid atmosphere. The use of the materials as an electrolyte in a laboratory-scale fuel cell and water vapor sensor has been demonstrated. Results for Ca-doped $LaNbO_4$ are given as examples.

11 Claims, 17 Drawing Sheets

U.S. PATENT DOCUMENTS

| | | | |
|---|---|---|---|
| 2002/0031694 A1* | 3/2002 | Van Berkel et al. | 429/30 |
| 2002/0187387 A1* | 12/2002 | Yadav et al. | 429/40 |
| 2003/0004051 A1 | 1/2003 | Kim | |
| 2003/0022048 A1* | 1/2003 | Meixner | 429/32 |
| 2004/0062968 A1* | 4/2004 | Tanner | 429/33 |

FOREIGN PATENT DOCUMENTS

| | | |
|---|---|---|
| EP | 0546871 | 6/1993 |
| FR | 2713218 | 6/1995 |
| GB | 2149120 | 6/1985 |
| JP | 52140500 | 11/1977 |
| JP | 58161924 | 9/1983 |
| JP | 62167206 | 7/1987 |
| JP | 2006-044990 | 2/1994 |
| JP | 9255953 | 9/1997 |
| JP | 9278521 | 10/1997 |
| JP | 2001-332454 | 11/2001 |
| JP | 2002-102427 | 4/2002 |
| RU | 1762523 | 4/1997 |
| WO | 8706574 | 11/1987 |
| WO | 03001623 | 1/2003 |
| WO | 2004085338 | 10/2004 |

OTHER PUBLICATIONS

Truls Norby, et al., Title: "Protonic Conduction in Acceptor-Doped Cubic Rate-Earth Sequioxides", Jr. Am. Ceram. Soc. 75[5] pp. 1176-1181 (1992).

Tetsuo Shimura, et al., Title: "Protonic Conduction in Lanthanum Strontium Aluminate and Lanthanum Niobate-Based Oxides at Elevated Temperatures", Solid State Ionics 154-155 (2002) pp. 653-658.

* cited by examiner

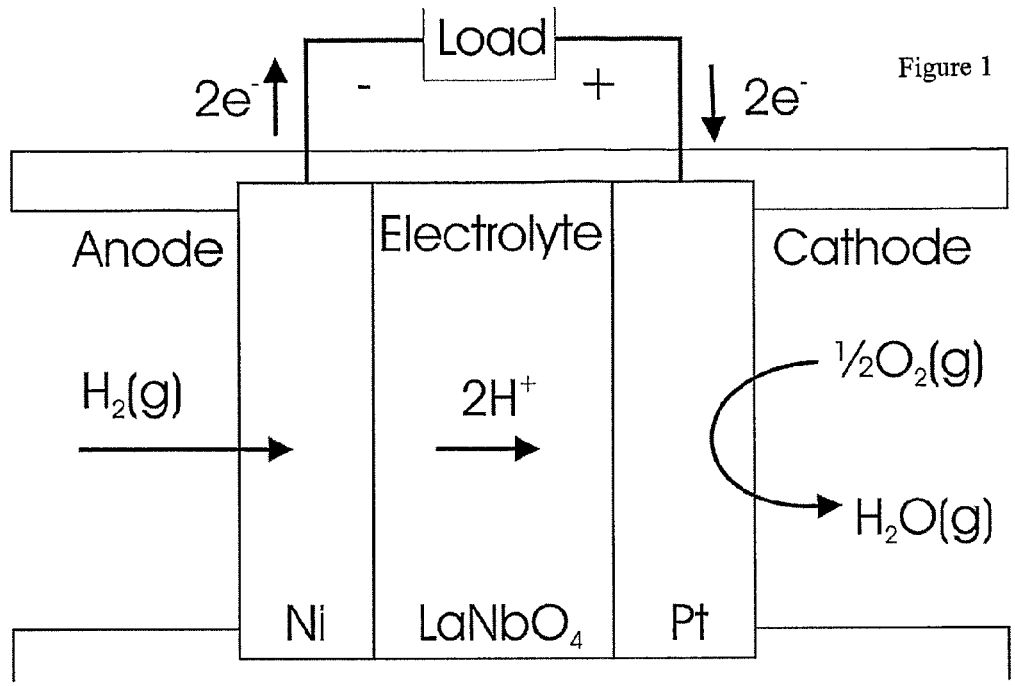
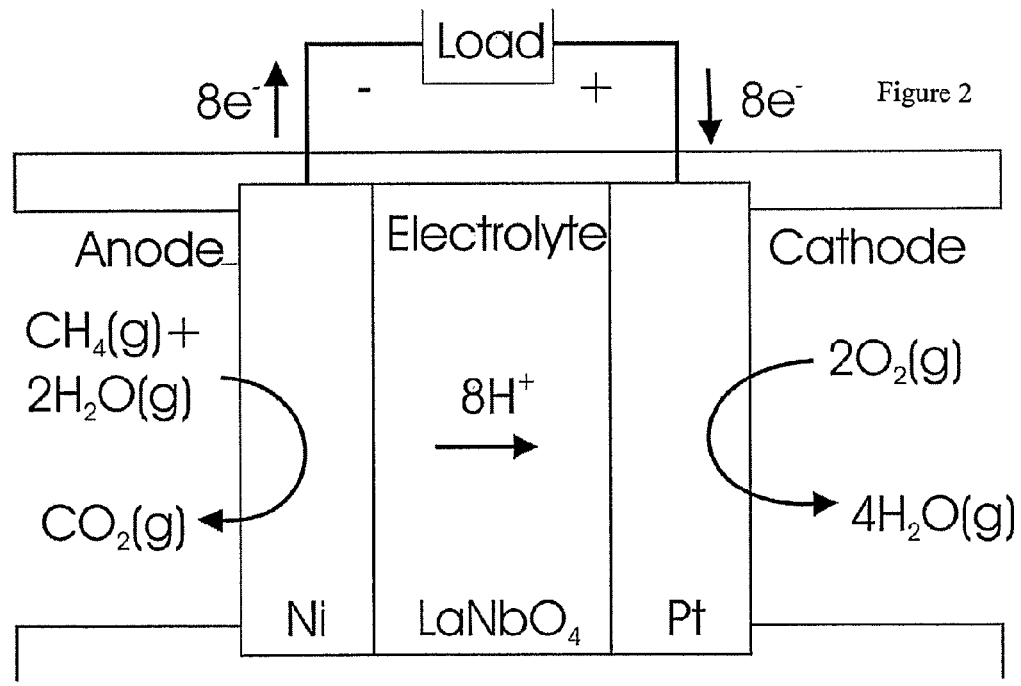

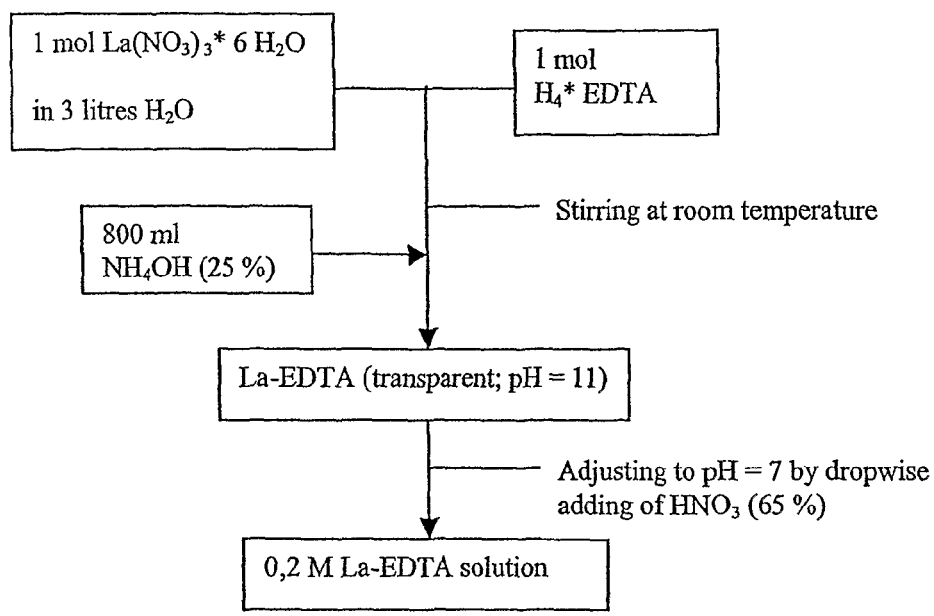
Figure 7. Flowchart for the preparation of La-EDTA solution

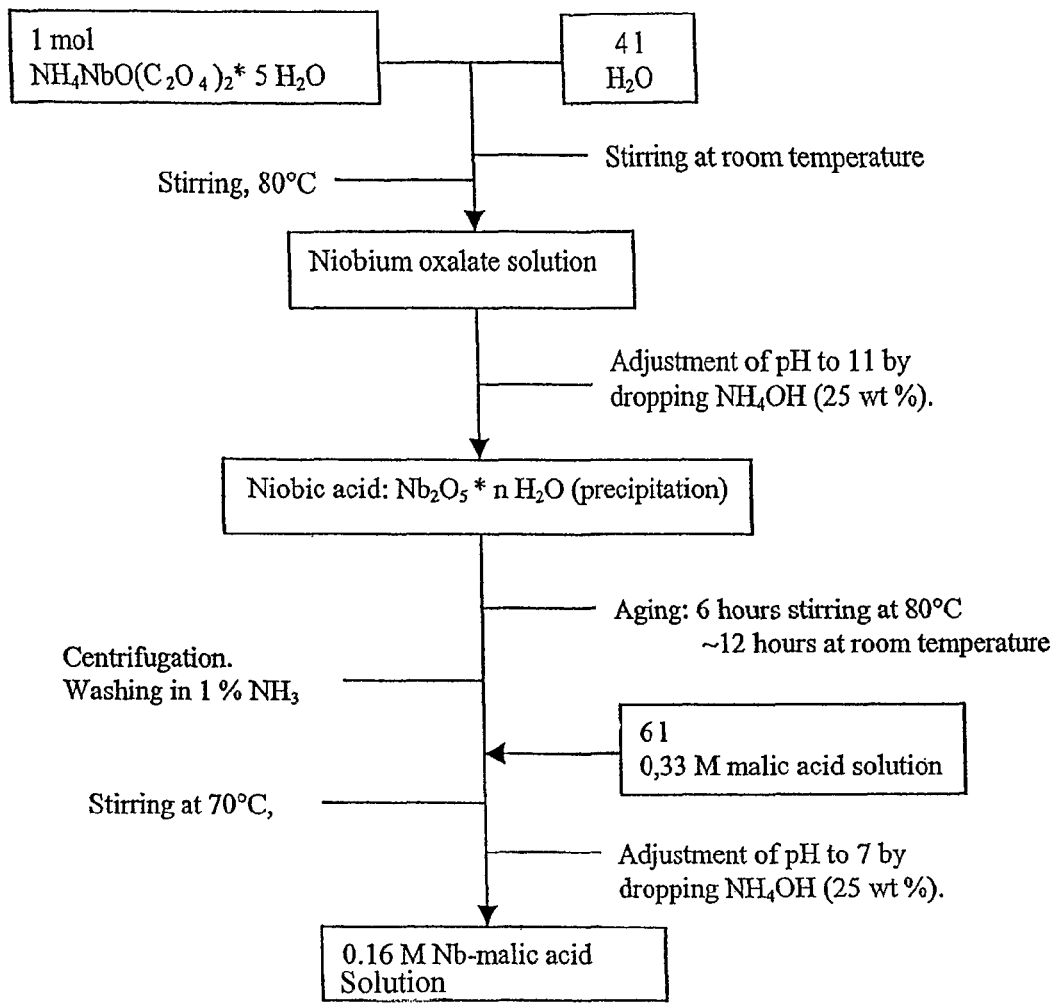
Figure 8. Flowchart for the preparation of Nb-malic acid solution

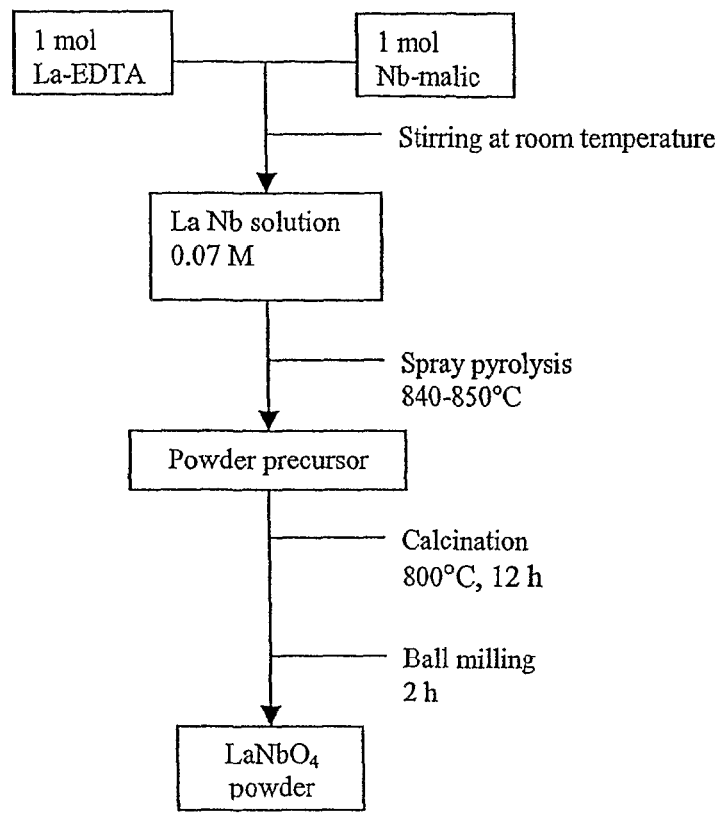
Figure 9. Flowchart for the preparation of LaNbO$_4$ from mixing the water-soluble compounds La-EDTA and Nb-malic.

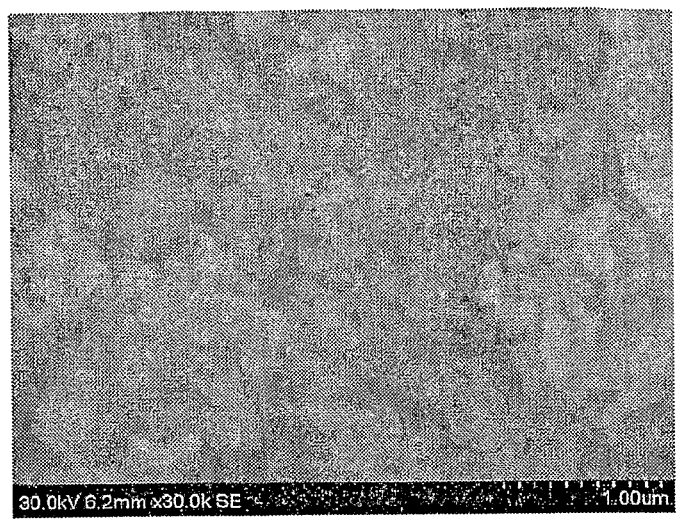
Figure 10. SEM image of LaNbO$_4$ precursor powder prepared by spray pyrolysis and thereafter calcined at 800°C in air for 6 hours.

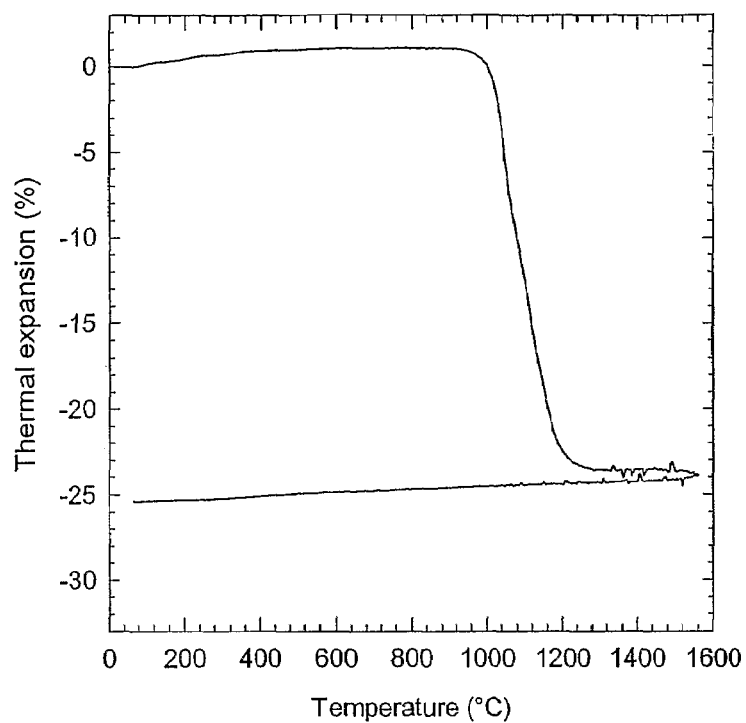
Figure 11. Dilatometer measurements of powder compacts of LaNbO$_4$ made from powder calcined at 800°C.

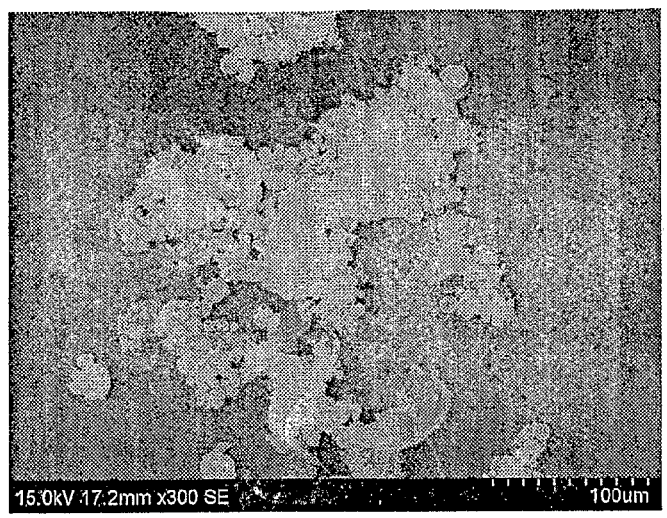
Figure 12. SEM image of $La_{0.995}Sr_{0.005}NbO_4$ precursor powder collected after the spray pyrolysis.

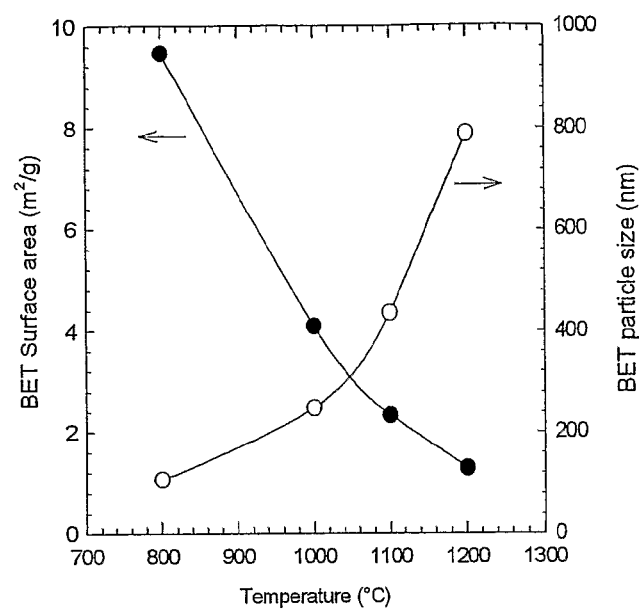
Figure 13 Surface area and particle size of $La_{0.995}Sr_{0.005}NbO_4$ powder calcined at different temperatures.

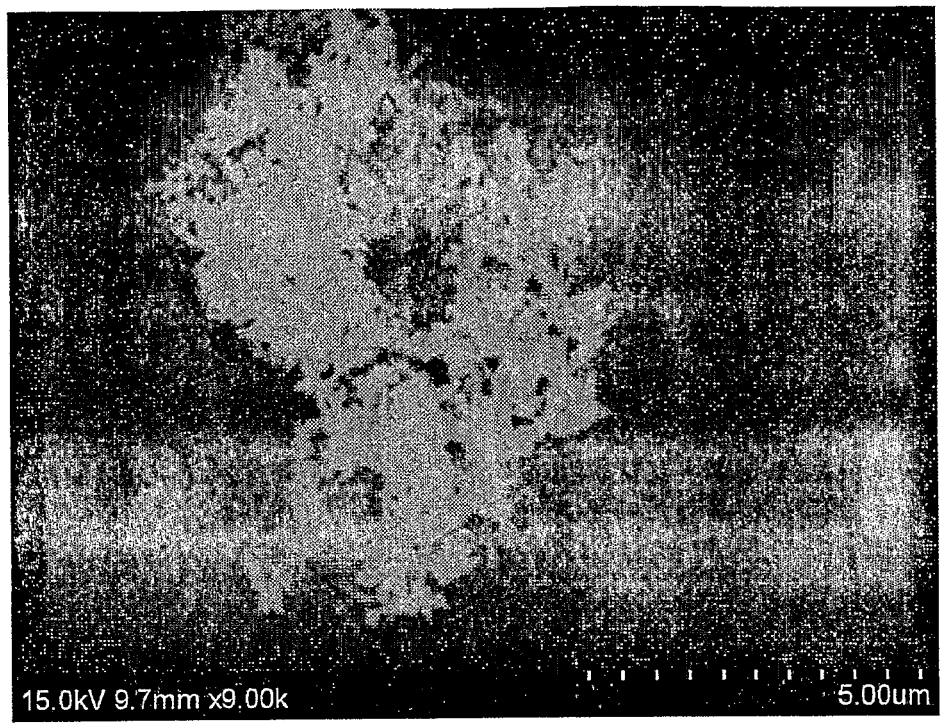
Figure 14. SEM image of $La_{0.995}Sr_{0.005}NbO_4$ powder calcined at 800°C for 12 h followed by milling for 2 hrs.

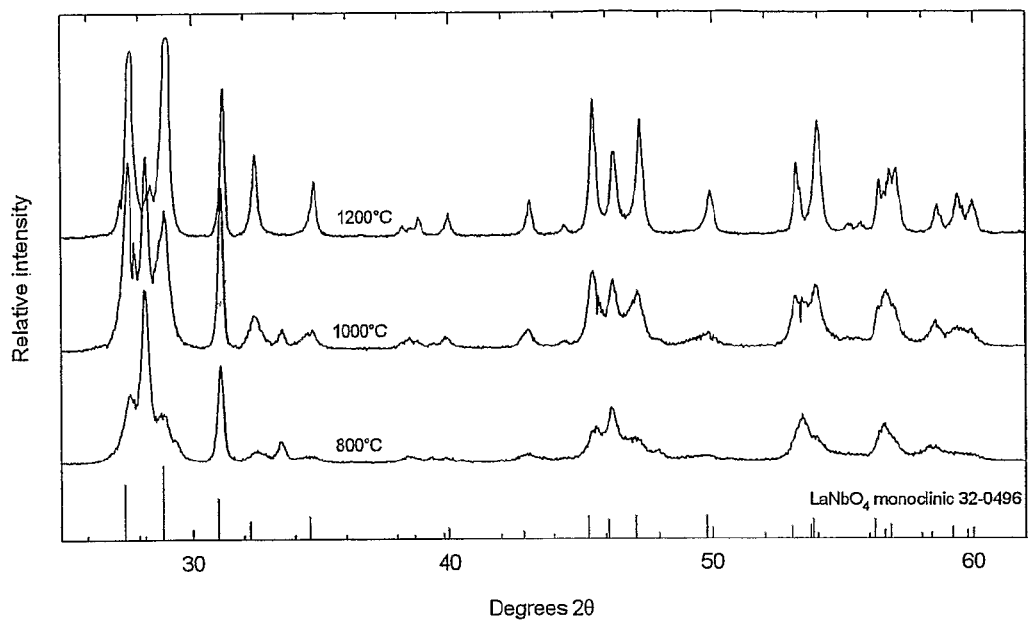
Figure 15. X-ray diffractograms of $La_{0.995}Sr_{0.005}NbO_4$ powders calcined at 800, 1000 and 1200 °C showing that the powders are single phase.

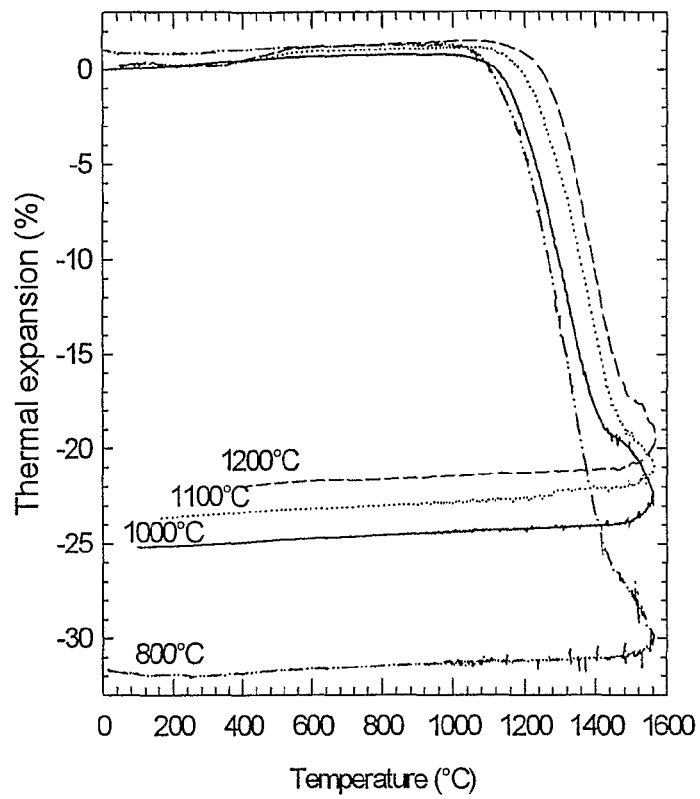
Figure 16. Dilatometer measurements of powder compacts of $La_{0.995}Sr_{0.005}NbO_4$ made from powder calcined at different temperatures.

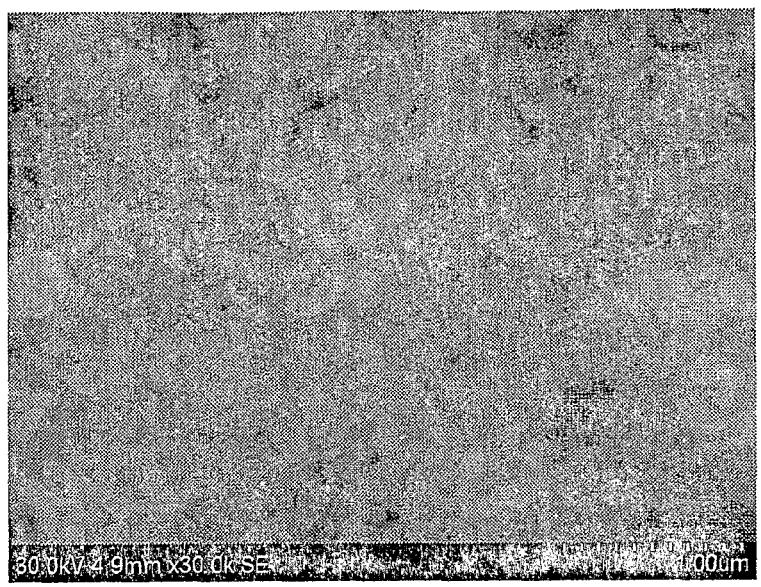
Figure 17. SEM image of $La_{0.98}Ca_{0.02}NbO_4$ powder calcined at 800°C for 6 h followed by milling for 2 hrs.

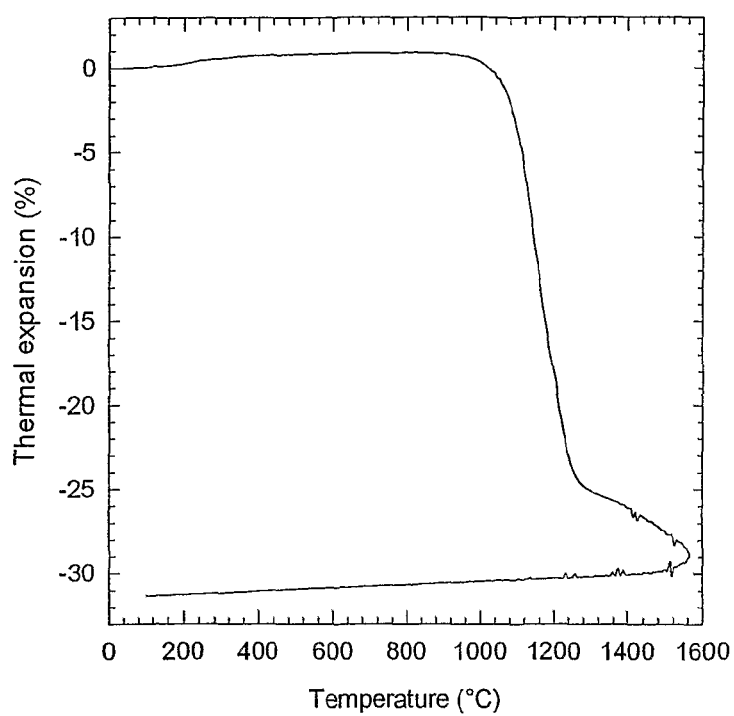
Figure 18. Dilatometer measurements of powder compacts of $La_{0.98}Ca_{0.02}NbO_4$ made from powder calcined at 800°C for 6 h.

PROTON CONDUCTORS

TECHNICAL FIELD

The present invention relates to new proton conducting, solid electrolytes in the form of rare earth orthoniobates or orthotantalates as well as to a new process for the manufacture thereof. The invention also relates to the use of the proton conducting electrolytes for manufacturing electrochemical cells, in particular fuel cells, electrolysers, electrochemical reactors, electrochemical pumps and sensors, and to the devices thus obtained.

BACKGROUND OF THE INVENTION

Electrochemical cells (fuel cells, electrolysers, sensors etc.) are a key element in the development of a more efficient and environmentally-friendly utilisation of fossil fuels, and in the development of systems for renewable energy based on hydrogen or a hydrogen carrier as storage medium for direct or indirect solar energy. Such cells need an ionically conducting or ion-conducting membrane (i.e. an electrolyte). This may be liquid (as in the lead-acid battery) or solid.

Solid electrolytes have many practical advantages over liquid based electrolytes as they allow, inter alia, greater energy density. To date, solid electrolytes have, for the most part, been based on oxygen ion conducting solid oxides which work at a high temperature (>600° C.) or on proton conducting polymeric electrolytes which only work at low temperatures (<100° C.). Devices made with the former electrolytes suffer from short lifetimes because of the high temperatures at which they are employed, whilst the latter electrolytes have problems with water balance and catalyst poisoning because of the low temperatures employed. Moreover, at present both technologies are costly.

Proton conducting oxides have recently emerged as a possible alternative to the electrolytes above and have shown high ionic conductivity at intermediate temperatures. However, these proton conducting oxides employ alkaline earth metals as principal components and are thus basic, which renders their use with fossil fuel impossible because of reaction with $CO_2$. There is thus a need to identify oxides which are less basic (e.g. which do not have alkaline or alkaline earth metals as principal components) and which have proton conductivity, and to demonstrate how this conductivity can be optimised and utilised.

Proton conductivity has previously been described at high and intermediate temperatures in a number of oxides and oxidic materials. As mentioned above, these include a number of Sr and Ba-containing oxides—primarily perovskites $AMO_3$ where A is Sr, Ba; M is Zr, Ce, Th, Ca+Nb or Sr+Nb (See Kreuer, "Proton conductivity; materials and applications", *Chem. Mater.*, 8 (1996) 610-641). Among materials that do not have alkaline earth metals as principal component, proton conductivity has been described in rare earth sesquioxides $Ln_2O_3$ where Ln is Y, La—Lu (See Haugsrud et al, "Proton conductivity of Ca-doped $Tb_2O_3$", submitted to *Solid State Ionics*), perovskites $AMO_3$ where A is La; M is Sc, Y, Er (See Larring et al "Protons in rare earth oxides", *Solid State Ionics*, 77 (1995) 147-51), pyrochlores $La_2Zr_2O_7$ (See Shimura et al *Solid State Ionics*, 86-88 (1996) 685-8), and orthophosphates $LnPO_4$ where Ln is La, Nd, Gd (See Norby et al, *Solid State Ionics*, 77 (1995) 240). However, the maximum proton conductivity has been more than an order of magnitude lower than that of the best Sr and Ba-containing materials, and some of the materials have limited stability at room temperature, others at operating conditions in fuel cells etc.

The object of the present invention is to provide new, improved materials which are suitable for use as proton conducting electrolytes, and which do not have the aforementioned disadvantages.

It has now surprisingly been found that doped rare earth orthoniobates and orthotantalates give an unexpectedly high proton conductivity and therefore are highly suitable as proton conducting electrolytes. This material group does not contain alkaline earth metals as principal components but are instead formed from a combination of a moderately basic rare earth oxide and an acidic Nb or Ta oxide, which gives good chemical stability. They have high melting points. Whilst certain doped orthoniobates and tantalates are known, e.g. as described in U.S. Pat. No. 6,620,750, never before have they been converted into proton conducting electrolytes.

SUMMARY OF THE INVENTION

Accordingly, the present invention provides a proton conducting electrolyte comprising an acceptor-doped rare earth orthoniobate or orthotantalate of formula $$Ln_{1-x}A_xM_{1-y}B_yO_4 \quad (I)$$

wherein Ln is an Y or La—Lu ion;
A is a metal ion having a valency less than that of metal Ln, e.g. an alkali or alkaline earth metal, such as Mg, Ca, Sr or Ba ion;
M is Nb or Ta;
B is a metal ion having a valency less than that of metal M, e.g. Mg, Sc, Al, Ti, Zr, Fe, Mn, Eu ion;
x=0-0.1, y=0-0.1, with the proviso that at least one of x or y is not 0;
wherein each constituent of the formula may also be present as a mixture of two or more of the named individual elements.

Alternatively viewed the invention provides a compound of formula (I')

$$Ln_{1-x}A_xMO_4 \quad (I')$$

wherein Ln is Y or La—Lu ion;
A is an alkaline earth metal ion, such as Mg, Ca, Sr or Ba ion;
M is Nb or Ta;
x=0.001-0.1;
wherein each constituent of the formula may also be present as a mixture of two or more of the named individual elements.

The acceptor-doped rare earth orthoniobate or orthotantalate preferably forms the principle component in the proton conductor. By principle component is meant that the acceptor-doped rare earth orthoniobate or orthotantalate forms the largest component present in the electrolyte (by weight). It is of course possible to use a mixture of rare earth orthoniobates or orthotantalates in which case it is the sum of rare earth orthoniobates or orthotantalates present which needs to form the principle component in the electrolyte. Thus, the amount of rare earth orthoniobate or orthotantalate in the electrolyte should be at least 50% wt thereof, preferably at least 70% wt, especially at least 90 wt %. Ideally, the electrolyte consists of one or more of the acceptor-doped rare earth orthoniobates or orthotantalates of the invention. Irrespective of the make up of the proton conductor, it is preferred if the acceptor-doped rare earth orthoniobate or orthotantalate is distributed throughout the electrolyte.

The metal M is preferably Nb. Ln may be yttrium or any element in the list La to Lu (i.e. elements 57 to 71). Ln is preferably La, Nd, Gd, Er, Tb or Y, especially La. The Ln material will preferably be in the 3+ oxidation state. The M ions will preferably be in the 5+ oxidation state. Whilst it is possible for each constituent of the formula (I) to be present as a mixture of two or more of the named individual elements (e.g. a mixture of Nb and Ta) it is preferred if Ln and M represent a single metal ion, especially La and Nb.

Doping metal ions A and B are in an oxidation state lower than that of the ion they are replacing. Thus, for "A" site doping metal ions, the preferred oxidation state is 2+ as these replace Ln which is in the 3+ oxidation state. For "B" site doping metal ions, preferred metal ions are in the 2+, 3+ or 4+ oxidation states, especially 3+ or 4+.

The term metal ion as used in the definitions of components A and B is intended to cover metals of appropriate valency in groups 1 to 12 as well as B, Al, Ga, In, Tl, Ge, Sn, Pb, Sb, Bi and Po. It is possible for doping metal ions A or B to be present on the "A" site (i.e. in place of Ln ions) or on the "B" site (i.e. in place of M ions) or both. It is preferred however, if doping occurs only on the "A" site. In this scenario, y is 0. Where B site doping occurs, B is preferably Mg, Sc, Al, Ti, Zr, Fe, especially titanium.

Preferred A site doping metal ions are alkaline earth metals, preferably selected from Ca, Mg or Sr, especially Ca or Sr.

The value of x and/or y may be between 0 and 0.1 with the proviso that at least one of x or y is not 0. Thus, at least one doping metal ion must be present in the electrolytes of the invention and the electrolyte cannot be $LnMO_4$ itself. Ideally, the value of x and/or y (if not 0) should be in the 0.001 to 0.1, preferably 0.002 to 0.08, especially 0.005 to 0.05. It should be stressed that the dopants replace metal ions in the crystal structure of the oxide in question. The concentration of doping metal ions should not be so high that an entire new phase of doping metal ion oxide forms.

Whilst it is possible for the A sites and B sites to comprise multiple doping metal ions, it is preferred if only one doping metal ion is present at each site. Most preferably, only one doping metal is present.

Lanthanide niobates and tantalates can be synthesised in the solid phase using techniques known in the art. Thus, suitable amounts of the requisite oxide or carbonate can be mixed, ground together and calcined. For example, a $Ln_2O_3$ oxide can be mixed with $M_2O_5$ and an amount of doping metal "A" and/or "B" carbonate (or optionally oxide). It is preferred if the amounts of material mixed are carefully measured to ensure that they are present in a stoichiometric amount. Thus, if the molar ratio of $Ln_2O_3$ to $ACO_3$ to $M_2O_5$ should be 0.99:0.01:1, the amounts of component mixed should reflect this stoichiometry.

Grinding of these materials is achieved conventionally, e.g. using an agate mill and is typically carried out in alcohol, e.g. isopropanol. This is removed prior to calcination. Calcination can take place at any useful temperature depending on the nature of the material, e.g. a temperature of from 800 to 1700° C. as is known in the art, e.g. 1000 to 1500° C. It is preferred if calcination is carried out until a single phase material is formed. This can be determined readily by X-ray diffraction analysis.

The resulting powder can be pressed and sintered to form the desired acceptor doped orthoniobate or orthotantalate electrolyte. Pressing and sintering can be carried out using known conditions. For example, pressing is typically carried out at ambient temperature in any standard press and sintering can occur at temperatures up to 1600° C., e.g. 800 to 1500° C., preferably 1000 to 1450° C., e.g. 1200° C. to 1400° C.

Solid phase synthesis gives rise to particles (presintering) of micron size and such particles are relatively difficult to sinter. Densification of the particles could be achieved more readily if particle sizes were lower.

The inventors have surprisingly found therefore that if the compounds of the invention are prepared by a spray pyrolysis technique, particle sizes in the nanometer range can be obtained. These particles are much easier to sinter and are therefore highly favoured. It is believed that this is the first time such small particles of orthoniobates and orthotantalates have been formed so these small particles as well as the particles formed by the process described below form a further aspect of the invention. This technique for the formation of orthoniobates and orthotantalates can be used on doped or non-doped orthoniobates and orthotantalates.

Thus, viewed from a further aspect the invention provides a process for preparing a compound of formula $LnMO_4$ (where Ln and M are as hereinbefore defined) or a doped derivative thereof, e.g. of formula (I) as hereinbefore described, comprising spray pyrolysing a solution comprising Ln ions and M ions, e.g. complexed Ln ions and M ions.

Viewed from another aspect the invention provides a compound of formula is $LnMO_4$ or doped derivative thereof prepared by the process as hereinbefore described.

The spray pyrolysis technique relies on the necessary metal ions being present in solution prior to spray pyrolysis. This is most easily accomplished by preparing a solution of each metal ion, mixing them and spray pyrolysing.

A solution of the lanthanide metal ion (Ln), e.g. lanthanum itself (La), can be prepared using any convenient counter ion (e.g. a nitrate) or using a complexing agent with appropriate solvent. Preferably, the solvent should be water. The Ln is preferably held in solution in the form of a complex, e.g. with a hexadentate, pentadentate, tetradentate, tridentate or bidentate ligand, in particular amino polycarboxylic acid chelating agents. Suitable ligands include EDTA, cyclohexanediamine tetraacetic acid (CDTA), DOTA, DTPA and ethylene diamine. EDTA is preferred.

Such a complex can be formed from any water soluble Ln precursor, e.g. its nitrate. This can be mixed with EDTA and basified, e.g. with ammonium hydroxide, to cause reaction between the Ln solution and EDTA. A pH of greater than 10 may be needed, e.g. 10.t to 11.5 e.g. around 11. The amount of complexing agent added will preferably be stoichiometric although a slight excess of complexing agent may be added. The resulting Ln EDTA solution can be stored however, since subsequent reaction with a solution of Nb or Ta ions preferably occurs at around pH 7 (e.g. pH 6 to 8), it will be convenient at this point to acidify the complex formed back to around pH 7 (e.g. using nitric acid).

A flow scheme of these reactions is shown in FIG. 7. It will be appreciated that any metal compound described herein may, in its crystalline form, possess water of crystallisation.

The Nb or Ta solution which needs to be mixed with the Ln solution can also be formed from any convenient solution although it is essential that the counter ion/complexing agent used with the Nb or Ta material does not form an insoluble salt with the Ln ions and vice versa. The solvent used for the Nb or Ta solution should be the same as that used for the Ln solution, i.e. preferably water.

A convenient commercially available starting material for the formation of an Nb solution is $NH_4NbO(C_2O_4)_2$. A soluble Ta oxalate is also commercially available. Unfortunately, Ln oxalates tend to be insoluble so this compound cannot be mixed with the Ln solution since Ln oxalates would precipitate. It is necessary therefore to remove to any traces of oxalate whilst still forming a soluble salt of the Nb ions.

This has been achieved be basifiying a solution of $NH_4NbO(C_2O_4)_2$ e.g. to around pH 11 (e.g. using ammonium hydroxide) which causes a form of niobic acid to precipitate. The basified solution of $NH_4NbO(C_2O_4)_2$ is aged at high temperature (e.g. 50 to 100° C.) for a few hours (e.g. 6 hours) and subsequently left at ambient temperature is for about twice the high temperature time (e.g. 12 hours) before the material is centrifuged in the presence of a base such as ammonia solution. The aging process is believed to cause the formation of the acid precipitate and agglomeration of the particles. Centrifugation in the presence of a base is a washing step carried out to remove oxalate ions. This washing step may be repeated a number of times to ensure that all oxalate is removed.

The solid material isolated from the centrifuge is free of oxalate as this is removed by the added base and may be redissolved in a multicarboxylated acid such as tartaric acid, citric acid or malic acid. Malic acid is preferred here. After stirring at high temperature, (e.g. 50 to 100° C.) a solution of Nb ions is formed. The pH of this solution can then be adjusted to pH 7 using acid for reaction with the Lu solution. Thus, the M ions may be held in solution in the form of a malic acid complex or other multicarboxlated acid complex.

There is a limit on the amount of multicarboxylated acid complex that will dissolve in water. For malic acid this is around 0.16 M. A scheme for this preparation is shown in FIG. 8. Whilst the formation of the M ions solution has been described in connection with Nb, the same principles would apply to the formation of a Ta solution.

The solutions of Ln and Nb/Ta can then be mixed in an appropriate ratio (depending on the molarity of each solution and the stoichiometry of the final product) and the solution which forms can be spray pyrolyzed. The pressure in the spray pyrolysis process may be in the range 1 to 2 bars. This can be achieved using a nozzle 0.5 to 1.5 mm, e.g. 1 mm in diameter. Atomization may occur into a rotating furnace at temperatures of from 600 to 1000° C., preferably 750 to 950° C., more preferably 800 to 900° C., especially 810 to 870° C. such as 830° C. Temperature should ideally be above 800° C.

The powder which exits the furnace (e.g. at a temperature of approximately 400 to 550° C.) can be collected in a cyclone and contains high levels of organics which can be removed by calcination (e.g. at 600 to 1000° C.). The formed powder can then be dry milled to reduce its volume and subsequently milled in alcohol with a suitable grinding media such as zirconia. FIG. 9 shows a flow scheme for these reactions.

Powders formed by this process are single phase and are typically submicron in size and non agglomerated. It has been surprisingly found that particle sizes can be controlled by the temperature at which calcination takes place, lower temperatures being associated with smaller particle sizes (See FIG. 13). Prior to calcination particle sizes are very low, e.g. of the order of 1 to 25 nm. Post calcination particles sizes increase to 10 to 1000 nm, preferably 100 to 800 nm, especially 200 to 600 nm in diameter.

Viewed from another aspect therefore the invention provides $LnMO_4$ or a doped derivative thereof having a particle size of less than 1000 nm, preferably less than 800 nm, especially less than 600 nm, most especially less than 100 nm, e.g. less than 25 nm.

Doping of the orthoniobates or tantalates formed by this spray pyrolysis process can be achieved readily be employing a soluble doping metal ion salt or complex in an appropriate amount. The soluble doping metal ion compound can be added into to either precursor solution or to the mixed solution prior to spray pyrolysis in an appropriate amount depending on the amount of doping meal ion which is desired to be present. It will obviously be necessary to reduce the amount of Ln or M solution to reflect the amount of A or B doping metal ion being added.

A convenient way of introducing the doping metal ions into solution is through their nitrates as these are often soluble in water. Thus, for a calcium doping metal ion, a solution of calcium nitrate can be added to the Ln complex. This can then be mixed as above with the Nb or Ta solution and spray pyrolyzed.

If multiple dopants are required, multiple soluble doping metal ion materials can be added.

To form the spray pyrolyzed powders into electrolytes it may be necessary to press and sinter the powders as previously described above. For these spray pyrolyzed materials sintering at greater than 1200° C. is ideal.

It is envisaged however, that to form a proton conducting electrolyte, it may be necessary to contact the sintered orthoniobates or tantalates with water (e.g. water vapour). Without wishing to be limited by theory, it is believed that during the synthesis of the doped $LnNbO_4$ and $LnTaO_4$ some $Ln^{3+}$ or $Nb/Ta^{5+}$ is substituted with an acceptor dopant, e.g. about 1 atomic % of the acceptor dopant. This is typically a material in a lower oxidation state that than metal which it substitutes, e.g. the 2+ oxidation state, e.g. $A^{2+}$ (A=Ca,Sr). This therefore results in an effectively negatively charged defect, which will be compensated by an effectively positively charged defect. In a dry atmosphere, this positively charged defect will normally be oxygen vacancies or electron holes. In the presence of water vapour however, the substances take up water, and the native charge compensating defects are suppressed and replaced by protons. These are located in hydroxide groups on oxygen ion sites in the oxide. At a high temperatures the protons are mobile, i.e. they jump from oxygen ion to oxygen ion, and the material becomes a proton conductor.

Thus, in a preferred embodiment, the formed doped orthoniobate and orthotantalate of the invention are exposed to water to ensure the presence of protons in the crystal structure. The amount of water needed is low however and sufficient water can be extracted from normal air.

It is also preferred if the electrolytes are employed in the presence of wet fuels (e.g. steam reformed fossil fuels).

Materials which transport protons are interesting for a number of low and high temperature industrial applications. Since hydrogen is one of the major chemical energy carriers, proton conductors can be utilised in processes related to conversion between chemical energy and electricity. This may for example be as purely ionic conductor serving as an electrolyte in a high temperature solid oxide fuel cell or as a mixed high temperature solid protonic-electronic conductor in a membrane for hydrogen separation.

It is a preferred feature of the invention that the electrolytes claimed can act as pure proton conductors or mixed conductors. It has also been noted that the claimed electrolytes are gas tight, i.e. they are impermeable to gas.

The acceptor doped compounds of the invention can therefore be employed in electrochemical cells, including fuel cells, electrolysers, electrochemical reactors, electrochemical pumps and sensors. They are also ceramic in nature and may be used as refractory materials. They may be ferroelastic. Ferroelastic properties are advantageous for structural applications since ferroelasticity induces a toughening effect. If they are doped with Eu, they may act as luminescent materials.

The present invention also comprises the use of the aforementioned proton conducting electrolytes for manufacturing electrochemical cells, including fuel cells, electrolysers, electrochemical reactors, electrochemical pumps and sensors, e.g. water sensor or hydrogen sensor.

The conductivity of selected representatives of the material group has been measured. It has been found that acceptor-doped representatives of the material group are pure proton conductors at temperatures of up to about 900° C. Moreover, the maximum proton conductivity obtained is higher than the best that is obtained for other groups of materials without Sr or Ba as principal component. Thus, these materials have potential applications in fuel cells were Sr or Ba based materials cannot be used in view of their reaction with carbon dioxide.

The proton conducting electrolytes of the invention can be used over a wide range of temperatures e.g. 600 to 1200° C.???, preferably around 700 to 900° C. The materials of the invention can also act as oxygen conductors (through p type electron conductivity) at higher temperatures, e.g. greater than 900° C.

The thickness of the electrolyte material employed in any device will depend upon the nature of the use to which the electrolyte is being put. However, in a fuel cell, the electrolyte may be of the order of 0.1 to 10 µm in thickness, e.g. 1 to 5 µm.

The use of the materials as proton conducting electrolytes has been demonstrated in a laboratory-scale fuel cell and water vapour sensor in the examples which follow.

In order to function as proton conductors, the sintered electrolytes may be provided with electrodes. These are typically transition metal materials such as Pt or Ni as is known in the art.

The invention will now be described further with reference to the following non-limiting examples and figures.

These and other features of the present application will become apparent to one of ordinary skill in the art upon review of the following detailed description when taken in conjunction with the drawing and appended claims.

BRIEF DESCRIPTION OF THE FIGURES

FIG. 1 shows the principle of a fuel cell with proton conducting acceptor-doped $LaNbO_4$ as electrolyte.

FIG. 2 shows the principle of another fuel cell with the same electrolyte.

FIG. 7 shows a flow scheme for the formation of La EDTA solution

FIG. 8 shows a flow scheme for the formation of Nb malic acid solution

FIG. 9 shows a flow scheme for the formation of $LaNbO_4$ by spray pyrolysis

FIG. 10. SEM image of $LaNbO_4$ precursor powder prepared by spray pyrolysis and thereafter calcined at 800° C. in air for 6 hours.

FIG. 11. shows dilatometer measurements of powder compacts of $LaNbO_4$ made from powder calcined at 800° C.

FIG. 12 shows an SEM image of $La_{0.995}Sr_{0.005}NbO_4$ precursor powder collected after spray pyrolysis FIG. 13 shows surface area and particle size of $La_{0.995}Sr_{0.005}NbO_4$ powder calcined at different temperatures.

FIG. 14. shows an SEM image of $La_{0.995}Sr_{0.005}NbO_4$ powder calcined at 800° C. for 12 h followed by milling for 2 hrs.

FIG. 15. shows an X-ray diffractograms of $La_{0.995}Sr_{0.005}NbO_4$ powders calcined at 800, 1000 and 1200° C. showing that the powders are single phase.

FIG. 16. shows dilatometer measurements of powder compacts of $La_{0.995}Sr_{0.005}NbO_4$ made from powder calcined at different temperatures.

FIG. 17 shows an SEM image of $La_{0.98}Ca_{0.02}NbO_4$ powder calcined at 800° C. for 6 h followed by milling for 2 hrs.

FIG. 18 shows dilatometer measurements of powder compacts of $La_{0.98}Ca_{0.02}NbO_4$ made from powder calcined at 800° C. for 6 h.

DETAILED DESCRIPTION OF THE INVENTION

FIGS. 1 and 2 show examples of fuel cells in which proton conducting acceptor-doped $LaNbO_4$ is used as electrolyte. FIG. 1 shows the principle of an $H_2$—$O_2$ fuel cell. The product, in this case pure water, is formed on the oxygen side when there is a pure proton conductor, so that circulation of the fuel will not be necessary. As examples of anode and cathode materials, Ni and Pt have been chosen here. Other materials can be implemented industrially.

Figure 3A:
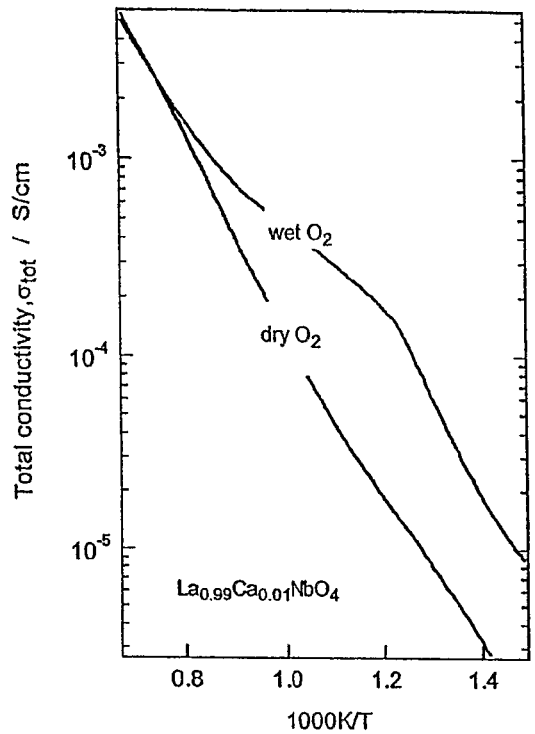
FIGS. 3a and b show total conductivity in Ca-doped $LaNbO_4$ as a function of inverse absolute temperature in oxygen and as a function of oxygen partial pressure.
Figure 3B:
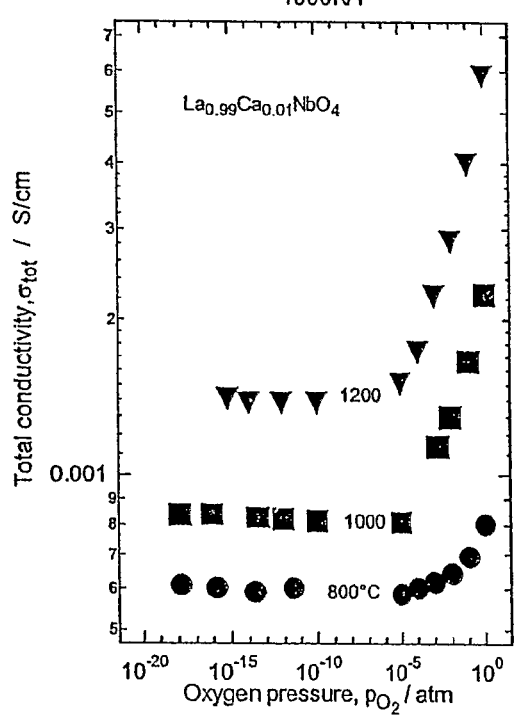

FIG. 3 shows total conductivity in Ca-doped $LaNbO_4$ as a function of inverse absolute temperature in oxygen (top half of the figure) and as a function of oxygen partial pressure at three temperatures (bottom half of the figure). The top half of the figure shows that the conductivity over a large temperature range is higher in wet oxygen than in dry oxygen, which indicates that proton conductivity dominates in this range. The bottom half of the figure shows that the conductivity is independent of oxygen partial pressure over a large range, which indicates ionic conductivity in this range. At higher oxygen partial pressure conductivity rises, typically for contributions from a p-type electronic conductivity.

Figure 4:
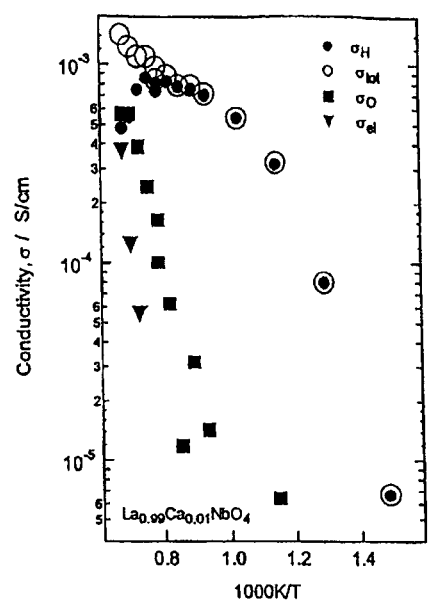
FIG. 4 shows total conductivity and partial conductivity in Ca-doped $LaNbO_4$ as a function of inverse absolute temperature.

FIG. 4 shows total conductivity and partial conductivity in Ca-doped $LaNbO_4$ plotted as a function of inverse temperature in humid atmosphere, based on measurements of transport numbers by measuring open voltage across concentration cells (the emf method). It can be seen that the material is a proton conductor over a large temperature range. The graph also demonstrates the material used as sensor in the range in question: the voltage across a sample between a reference gas and an unknown gas will give unambiguous information about the hydrogen activity in the unknown gas.

Figures 5A, 5B:
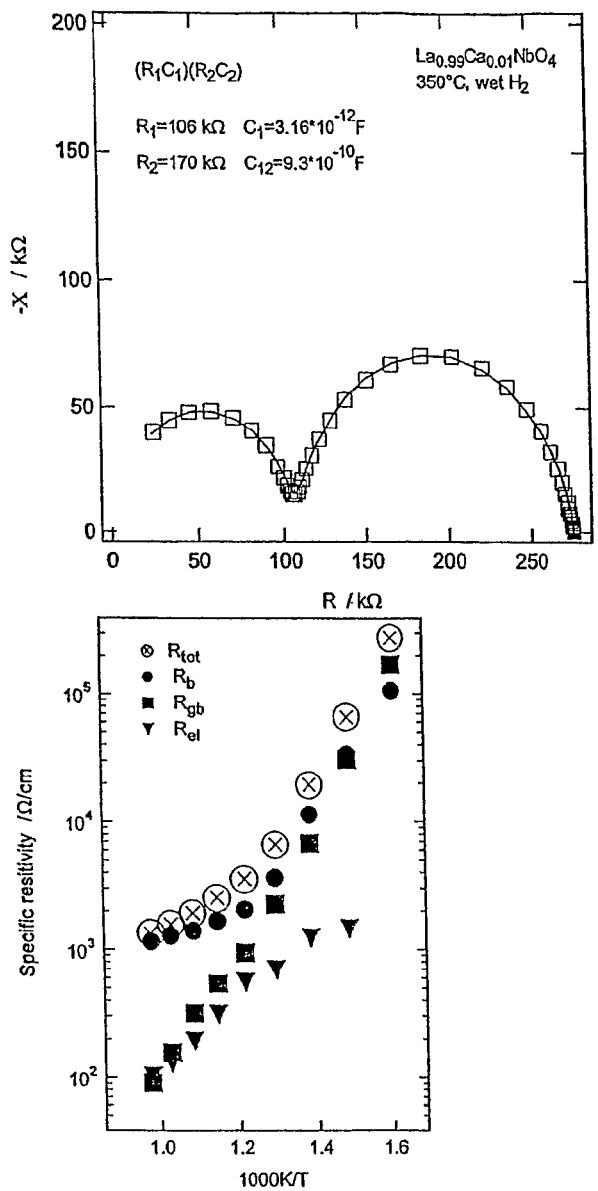
FIGS. 5a and b show an impedance spectrum of Ca-doped $LaNbO_4$ and deconvoluted impedances versus inverse absolute temperature, based upon such spectra.

FIG. 5 shows the impedance spectrum of Ca-doped $LaNbO_4$, which shows that the material has impedance from bulk and from grain boundaries. The bottom half of the figure shows how total resistivity in the sample, from impedance spectroscopy, can be divided up into contributions from bulk (b), grain boundaries (gb) and electrodes (el) as a function of inverse absolute temperature.

Figure 6:
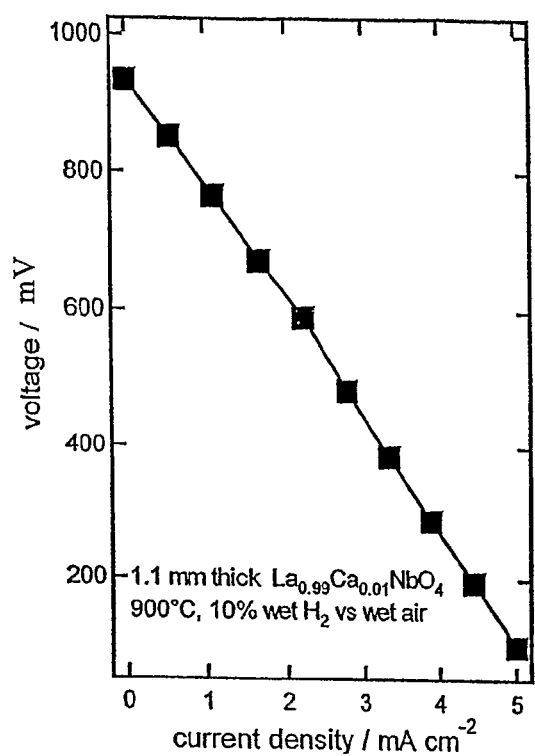
FIG. 6 shows voltage as a function of current density for a laboratory-scale fuel cell with an electrolyte of Ca-doped $LaNbO_4$.

FIG. 6 shows a graph of voltage as a function of current density for a laboratory-scale fuel cell with a thick (1.1 mm) electrolyte of Ca-doped $LaNbO_4$. The cell was run with wet 10% $H_2$ as fuel and wet air as oxidant, at 900° C. Open cell voltage is about 0.93 V. The current density is about 1.5 mA/cm$^2$ at 0.7 V cell voltage, which gives about 1 mW/cm$^2$ power density. This shows that a cell with an electrolyte of 1-5 µm thickness would be able to give power densities of practical interest (200-1000 mW/cm$^2$).

Example 1

General Protocol for Solid Phase Synthesis

The proton conducting oxides are synthesised by mixing selected amounts of $Ln_2O_3$ (Ln=Y, La, Nd, Gd, Tb, Er), $M_2O_5$ (M=Nb, Ta) and $ACO_3$ (A=Ca, Sr, Ba) according to desired stoichiometry $Ln_{1-x}A_xMO_4$. The mixture was ball-ground in an agate mill with isopropanol, the alcohol was evaporated and the mixture was calcined at up to 1300° C. This was repeated until the material was phase-pure according to X-ray diffraction (XRD). A tablet was then cold-pressed and sintered at up to 1600° C.

The materials produced in this fashion are described in Table 1:

TABLE 1

| A-Site | | B-site | | A-site doping | | | B-site doping |
|---|---|---|---|---|---|---|---|
| type | amount | type | amount | Ca | Sr | Ba | Ti |
| La | 0.995 | Nb | 1 | 0.005 | | | |
| La | 0.99 | Nb | 1 | 0.01 | | | |
| La | 0.98 | Nb | 1 | 0.02 | | | |
| La | 0.95 | Nb | 1 | 0.05 | | | |
| La | 0.995 | Nb | 1 | | 0.005 | | |
| La | 0.993 | Nb | 1 | | 0.007 | | |
| La | 0.99 | Nb | 1 | | 0.01 | | |
| La | 0.98 | Nb | 1 | | 0.02 | | |
| La | 0.96 | Nb | 1 | | 0.04 | | |
| La | 0.95 | Nb | 1 | | 0.05 | | |
| La | 0.92 | Nb | 1 | | 0.08 | | |
| La | 0.99 | Nb | 1 | | | 0.01 | |
| La | 0.98 | Nb | 1 | | | 0.02 | |
| Nd | 0.99 | Nb | 1 | 0.01 | | | |
| Nd | 0.99 | Nb | 1 | | 0.01 | | |
| Nd | 1 | Nb | 0.95 | | | | 0.05 |
| Gd | 0.95 | Nb | 1 | 0.05 | | | |
| Tb | 0.98 | Nb | 1 | 0.02 | | | |
| Er | 0.99 | Nb | 1 | 0.01 | | | |
| Er | 0.99 | Nb | 1 | | 0.01 | | |
| Y | 0.99 | Nb | 1 | 0.01 | | | |
| La | 0.99 | Ta | 1 | 0.01 | | | |
| Nd | 0.99 | Ta | 1 | 0.01 | | | |
| Gd | 0.99 | Ta | 1 | 0.01 | | | |
| Er | 0.99 | Ta | 1 | 0.01 | | | |

Example 2

Electrodes of commercial Pt paste or own-produced Ni+electrolyte cremate paste were applied to sintered material 2 ($La_{0.99}Ca_{0.01}NbO_4$) of table 1. The sample provided with electrodes was mounted in a measuring cell where the electrodes were contacted by Pt wires. The electrodes were supplied with two different gases, where the sample separates the two gases by means of a gold seal, and where the cell can be heated up to 1300° C. in a tube furnace, controlled by a thermo element close to the sample. The gases that are added are mixed in a special gas mixer described in T. Norby, "EMF Method Determination of Conductivity Contributions from Protons and Other Foreign Ions in Oxides", *Solid State Ionics*, 28-30 (1988) 1586-91.

The total conductivity in the sample was measured using an impedance spectrometer, which also can distinguish between electrode impedance, grain boundary impedance and bulk impedance; reference is made to FIG. 5.

The partial proton conductivity (the transport number of protons) is measured by measuring the voltage across the sample when it is subjected to a gradient in hydrogen activity; in this connection reference is made to FIG. 4.

The use as sensor is demonstrated by the voltage which arises when the sample is subjected to a reference gas on the one hand and a gas with unknown hydrogen activity on the other. Reference is made again to FIG. 4 as regards this use.

The use as a fuel cell is demonstrated by the voltage that arises when the sample is exposed to $H_2$ and $O_2$ and current is drawn from the cell using a potensiostat/galvanostat. In this connection, reference is made to FIG. 6.

The novel proton conducting electrolytes according to the present invention could advantageously be used in fuel cells and electrolysers where the electrolyte can be used as a thin film applied to a supporting porous electrode.

Example 3

Manufacture of Lanthanum Niobate by Spray Pyrolysis (I) La EDTA Solution:

Lanthanum nitrate, $La(NO_3)_3 \cdot 6H_2O$ (1 mol) (Fluka, >99%), dissolved in 3 litres of water was mixed with ethylenediaminetetraacetic acid ($H_4 \cdot EDTA$) (1 mol) (Acros Organics, 99%), with stirring. 800 ml ammonium hydroxide, $NH_4OH$ (25%) was added to the colloid solution to form water-soluble La-EDTA complex. pH was adjusted to 7 by adding nitric acid, $HNO_3$ (65%) drop by drop, and the solution was filtered.

(II) Nb Malic Acid Solution

Ammonium niobium dioxalate oxide pentahydrate, $(NH_4)NbO(C_2O_4)_2 \cdot 5H_2O$ (1 mol) (H. C. Starck), was dissolved in 4 litres of water. $NH_4OH$ (25 wt %) was dropped during stirring until pH=11, precipitating niobic acid, $Nb_2O_5 \cdot nH_2O$. The mixture was heated at 80° C. for 6 hours while stirring, followed by 12 hours of aging without heating or stirring. The precipitate was washed in $NH_4OH$ (1%) by centrifugation to eliminate oxalate ions. After washing the precipitated niobic acid was dissolved in DL-malic acid solution, MA (0.33 M) (Aldrich, 99%). The molar ration of [MA]:[Nb]=2:1. The mixture was heated at 70° C. to dissolve all $Nb_2O_5 \cdot nH_2O$, and filtered. pH in the solution was adjusted to 7 by dropping $NH_4OH$ (25 wt %). The concentration of the solutions was measured by thermogravimetric analysis.

(III) Lanthanum Niobate

The La-EDTA solution (from (I)) was mixed with the Nb-malic acid solution (II) in the molar ratio of [La]:[Nb]=1:1 just prior to spray pyrolysis. The pH of both solutions is approximately 7 before the mixing to avoid precipitation. The solution containing La and Nb was spray pyrolyzed using a home-made pilot scale equipment. A two phase nozzle with 1.5 bar pressurized air was used to atomize the solution at a rate of 2 liters per hour. The diameter of the nozzle was 1 mm. The solution was atomized directly into a rotating furnace keeping a temperature in the range 840 to 850° C. Outlet temperature of the furnace was 450-500° C. The product called powder precursor was collected in a cyclone. The resulting very fine powder precursor contained about 25% organics which was removed by calcining at 800° C. for 6 to 12 hours. Prior to the calcination, the powder was dry milled for 5 min to reduce the volume. The resulting $LaNbO_4$ powder was milled for 2 hours in ethanol with zirconia as grinding media. The resulting powder was submicron non-agglomerated powder of single phase $LaNbO_4$ as shown in FIG. 10. The prepared fine powder shows excellent sintering properties as can be seen from the onset of sintering at approximately 1000° C. in FIG. 11 which shows the dilatometer (Netzsch, DIL402C) results.

Example 4

Doping Using Spray Pyrolysis

A part of the lanthanum was substituted with strontium to form $La_{0.995}Sr_{0.005}NbO_4$. This was done by adding 0.5 wt % dried strontium nitrate, $Sr(NO_3)_2$ (Merck, 99%), to the La-EDTA solution after standardisation and reducing the amount of La-EDTA solution correspondingly. The rest of the synthesis was performed as described in Example 3. A SEM image (Hitachi, S-3400N) of the powder precursor is presented in FIG. 12 and shows a fine delicate structure of shells from the dried atomized droplets.

After calcinations in ambient air to 800° C., the surface area of the powder is almost 1000 m²/g measured by $N_2$ adsorption (Micromeritics, ASAP 2000) and the mean particle size calculated from the surface area is approximately 100 nm as can be seen from FIG. 13. The surface area is decreasing and particle size is increasing with calcination temperature up to 1200° C. A SEM image of the powder after calcination to 800° C. is shown in FIG. 14. The prepared fine powder which is single phase (FIG. 15) shows excellent sintering properties as can be seen from the onset of sintering at approximately 1200° C. in FIG. 16 which shows the dilatometer (Netzsch, DIL402C) results for powders prepared using different calcinations temperatures. Full density can be achieved during sintering at 1400° C. for 2 hours giving a homogeneous microstructure.

Example 5

Doping Using Spray Pyrolysis

A part of the lanthanum was substituted with calcium to form $La_{0.98}Ca_{0.02}NbO_4$. This was done by adding 2 wt % dried calcium nitrate, $Ca(NO_3)_2$ (Merck, 99%), to the La-EDTA solution after standardisation and reducing the amount of La-EDTA solution correspondingly. The rest of the synthesis was performed as described in Example 3.

A SEM image (Hitachi, S-3400N) of the powder after calcinations to 800° C. for 6 hours is presented in FIG. 17 and shows a fine particle size. The prepared fine powder shows excellent sintering properties as can be seen from the onset of sintering at approximately 1050° C. in FIG. 18 which shows the dilatometer (Netzsch, DIL402C) results.

It should be apparent that the foregoing relates only to the preferred embodiments of the present application and that numerous changes and modification may be made herein by one of ordinary skill in the art without departing from the general spirit and scope of the invention as defined by the following claims and the equivalents thereof.

We claim:

1. A fuel cell or a sensor with a proton conducting electrolyte comprising an acceptor-doped rare earth orthoniobate or orthotantalate of formula (I)

$$Ln_{1-x}A_xM_{1-y}B_yO_4 \quad (I)$$

wherein Ln is Y or La—Lu ion;
A is Mg, Ca or Sr metal ion having a valency less than that of metal Ln;
M is Nb or Ta;
B is Mg, Sc, Al, Ti, Zr, Fe, Mn, or Eu having a valency less than that of metal M;
x=0.001-0.1, y=0-0.1, with the proviso that at least one of x or y is not 0;
wherein each constituent of the formula may also be present as a mixture of two or more of the named individual elements.

2. A fuel cell or a sensor with a proton conducting electrolyte according to claim 1 wherein Ln is a Y, La, Nd, Gd, Tb, or Er ion.

3. A fuel cell or a sensor with a proton conducting electrolyte according to claim 1 wherein B is Mg, Sc, Al, Ti, Zr, or Fe.

4. A fuel cell or a sensor with a proton conducting electrolyte according to claim 1 wherein B is Ti.

5. A fuel cell or a sensor with a proton conducting electrolyte according to claim 1 wherein y is 0.

6. A fuel cell or a sensor with a proton conducting electrolyte according to claim 1 wherein Ln is La.

7. A fuel cell or a sensor with a proton conducting electrolyte according to claim 1 wherein M is Nb.

8. A fuel cell or a sensor with a proton conducting electrolyte according to claim 1 wherein said acceptor-doped rare earth orthoniobate or orthotantalate forms the principle component of said electrolyte.

9. A fuel cell or sensor with an acceptor-doped rare earth orthoniobate or orthotantalate compound of formula (I')

$$Ln_{1-x}A_xMO_4$$

Wherein Ln is Y or La—Lu ion;
A is Mg, Ca, or Sr;
M is Nb or Ta;
x=0.001-0.1;
wherein each constituent of the formula may also be present as a mixture of two or more of the named individual elements.

10. A fuel cell or a sensor with a proton conducting electrolyte as claimed in claim 1 comprising an acceptor-doped rare earth orthoniobate or orthotantalate of formula (I):

$$Ln_{1-x}A_xM_{1-y}B_yO_4 \quad (I)$$

wherein Ln is a Y, La, Nd, Gd, Tb or Er ion;
A is a Ca, Sr or Ba metal ion having a valency less than that of metal Ln;
M is Nb or Ta;
B is Ti having a valency less than that of metal M;
x=0.001-0.1, y=0-0.1, with the proviso that at least one of x or y is not 0.

11. A fuel cell or a sensor with a proton conducting electrolyte according to claim 1 wherein each constituent of the formula may also be present as a mixture of two or more of the named individual elements.

* * * * *